United States Patent [19]

Shen et al.

[11] 4,087,549
[45] May 2, 1978

[54] SULPHONIC ACID CONTAINING INDENYL DERIVATIVES

[75] Inventors: Tsung-Ying Shen, Westfield; Howard Jones, Holmdel, both of N.J.

[73] Assignee: Merck & Co., Inc., Rahway, N.J.

[21] Appl. No.: 752,647

[22] Filed: Dec. 20, 1976

Related U.S. Application Data

[63] Continuation-in-part of Ser. No. 539,377, Jan. 8, 1975, abandoned, which is a continuation-in-part of Ser. No. 312,549, Aug. 6, 1972, Pat. No. 3,860,636.

[51] Int. Cl.$^2$ .................... A01N 9/00; C07C 143/24
[52] U.S. Cl. .................................. 424/315; 260/505 R
[58] Field of Search .............. 424/303, 315, 335, 337; 260/505 R, 505 C

[56] References Cited

U.S. PATENT DOCUMENTS 3,312,730   4/1967   Winter et al. .................... 260/473

*Primary Examiner*—A. Siegel
*Attorney, Agent, or Firm*—Raymond M. Speer; Thomas E. Arther; Mario A. Monaco

[57] ABSTRACT

New substituted indenyl methyl sulfonic acids and derivatives thereof which have anti-inflammatory, antipyretic and analgesic activity. Also included are methods of preparing said indenyl compounds, pharmaceutical compositions having said indenyl compounds as an active ingredient and methods of treating inflammation by administration of said indenyl compounds.

12 Claims, No Drawings

SULPHONIC ACID CONTAINING INDENYL DERIVATIVES

RELATED CASES

This application is a continuation-in-part of U.S. application Ser. No. 539,377 filed Jan. 8, 1975 now abandoned, which in turn was a continuation-in-part of U.S. application Ser. No. 312,549, filed Dec. 6, 1972 now U.S. Pat. No. 3,860,636.

SUMMARY OF THE INVENTION

This invention relates to new substituted 1-Ar-alkylidene (or heteroalkylidene) indenyl methyl sulfonic acids and derivatives thereof to processes for producing the same. This invention also relates to pharmaceutical compositions containing said indenyl compounds as an active ingredient and to methods of treating pain, fever or inflammation by administering these particular compounds to patients.

DESCRIPTION AND PREFERRED EMBODIMENTS

The invention is more particularly directed to new substituted indenyl compounds having the following general formula:

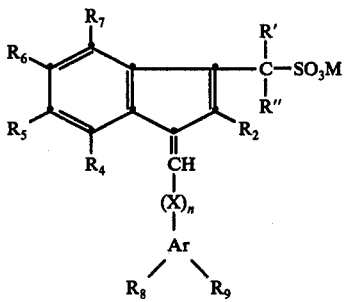

wherein:
$R_2$ may be hydrogen, alkyl, haloalkyl, alkenyl, alkynyl or trihalomethyl;
$R_4$, $R_5$, $R_6$, $R_7$, $R_8$ and $R_9$ each may be hydrogen, alkyl, acyloxy, aryloxy, alkoxy, nitro, amino, acylamino, alkylamino, dialkylamino, alkenyl, alkynyl, alkenyloxy, dialkylaminoalkyl, sulfamyl, alkylthio, alkylsulfinyl, alkylsulfonyl, hydroxy, hydroxyalkyl, acyl, halo, cyano, carboxy, carboalkoxy, carbamido, haloalkyl, cycloalkyl, trifluoromethyl, aroyl or cycloalkyloxy;
X may be alkylene, alkenylene, alkynylene, O, S, carbonyl or NR wherein R is hydrogen or alkyl;
n is 0 or 1;
Ar may be aryl or heteroaryl;
M may be hydrogen, alkyl or a cation; and
R' and R" each may be hydrogen, alkyl, aryl, alkylthio, hydroxy, alkoxy, halogen or to ether a carbonyl.

The aryl or heteroaryl substituent, Ar, may include an aryl ring system such as benzene, naphthalene or biphenyl or a heteroaryl ring system such as a pyrrole, furan, thiophene, pyridine, imidazole, pyrazine, thiazole, pyrimidine, benzothiazole, pyrazole, oxazole, pyrane, pyridazine, indole, thionaphthene, benzofuran, benzimidazole, azaindole, benzoxyrane, quinoline, isoquinoline, quinoxaline, naphthyridine or benzoxazole and may be substituted with any of the aforementioned $R_8$ and $R_9$ substituents.

In the preferred compounds of this invention, $R_2$ is hydrogen, $C_{1-5}$ loweralkyl or $C_{1-5}$ chloro, bromo, or fluoro loweralkyl; $R_4$, $R_5$, $R_6$ and $R_7$ may be hydrogen, halo (chloro, bromo, fluoro), $C_{1-5}$ loweralkyl, halo $C_{1-5}$ lower-alkyl, $C_{1-5}$ loweralkoxy, cyano, nitro, amino, $C_{1-5}$ lower-alkylamino, $C_{1-5}$ diloweralkylamino, $C_{1-5}$ loweralkanoyloxy, $C_{1-5}$ loweralkanoylamino, hydroxy, $C_{1-5}$ loweralkanoyl, $C_{2-5}$ loweralkenoyl, $C_{2-5}$ loweralkenyloxy or trifluoromethyl; $R_8$ and $R_9$ are each hydrogen, chloro, bromo, fluoro, $C_{1-5}$ loweralkylthio, $C_{1-5}$ loweralkyl, trifluoromethyl, $C_{1-5}$ loweralkylsulfonyl, $C_{1-5}$ loweralkylsulfinyl, $C_{1-5}$ diloweralkylsulfamyl, nitro or $C_{1-5}$ loweralkoxy; X is $C_{1-4}$ alkylene, $C_{2-4}$ alkenylene, $C_{2-4}$ alkynylene or -O-; n is 0 or 1; Ar is the phenyl; R' and R" may each be hydrogen or $C_{1-5}$ loweralkyl; and M is hydrogen or $C_{1-5}$ loweralkyl, and especially hydrogen.

In the most preferred aspect of this invention, $R_2$ is hydrogen or $C_{1-5}$ loweralkyl; $R_4$, $R_5$, $R_6$ and $R_7$ are each hydrogen, chloro, bromo, fluoro, $C_{1-5}$ loweralkyl, $C_{1-5}$ loweralkoxy, nitro, amino, $C_{1-5}$ loweralkylamino, halo $C_{1-5}$ loweralkyl, $C_{1-5}$ diloweralkylamino, $C_{2-5}$ loweralkanoylamino, hydroxy, $C_{1-5}$ loweralkanoyloxy or trifluoromethyl, at most only 2 of $R_4$, $R_5$, $R_6$ or $R_7$ being other than hydrogen at any one time; $R_8$ and $R_9$ are each hydrogen, $C_{1-5}$ loweralkyl, $C_{1-5}$ loweralkyloxy, $C_{1-5}$ loweralkylsulfinyl, $C_{1-5}$ loweralkylsulfonyl, chloro, bromo, fluoro, $C_{1-5}$ loweralkylsulfamyl, $C_{1-5}$ diloweralkylsulfamyl or nitro; X is $C_{1-4}$ alkylene, $C_{2-4}$ alkenylene, $C_{2-4}$ alkynylene or —O—; n is 0 or 1; Ar is phenyl; R' and R" are each hydrogen; and M is hydrogen.

Within the most preferred aspect of this invention, it has been found that certain of the compounds of this invention are especially useful. These compounds are where $R_2$ is hydrogen or $C_{1-5}$ loweralkyl; $R_4$, $R_5$, $R_7$ and $R_8$ are each hydrogen; $R_6$ is hydrogen, halo, $C_{1-5}$ loweralkyl, $C_{1-5}$ loweralkoxy, $C_{1-5}$ diloweralkylamino, or hydroxy; $R_9$ is hydrogen, chloro, bromo, fluoro, $C_{1-5}$ loweralkylthio, or $C_{1-5}$ loweralkylsulfinyl; X is —O—; n is 0; Ar is phenyl; R' and R" are each hydrogen; and M is hydrogen.

This invention also relates to a method of treating pain, fever or inflammation in patients using a compound of Formula I, particularly and especially the preferred compounds as the active constituent.

The compounds of the instant invention can be used to treat inflammation by reducing inflammation and relieving pain in such diseases as rheumatoid arthritis, osteoarthritis, gout, infectious arthritis and rheumatic fever. The compounds of Formula I can also be used as an anti-pyretic and would be administered and used in the same manner and in same dosage ranges as if they were being used to treat inflammation as discussed further on.

The treatment of inflammation in accordance with the method of the present invention is accomplished by topically, orally, rectally or parenterally administering to patients a composition of a compound of Formula I, particularly the especially preferred compounds in a non-toxic pharmaceutically acceptable carrier.

The non-toxic pharmaceutical carrier may be, for example, either a solid or a liquid. Exemplary of solid carriers are lactose, corn starch, gelatin, talc, sterotix, stearic acid, magnesium stearate, terra alba, sucrose, agar, pectin, cab-o-sil and accacia. Exemplary of liquid carriers are peanut oil, olive oil, sesame oil and water.

Similarly, the carrier or diluent may include a time delay material such as glyceryl monosterate or glyceryl distearate alone or with a wax.

Several pharmaceutical forms of the therapeutically useful compositions can be used. For example, if a solid carrier is used, the compositions may take the form of tablets, capsules, powders, troches or lozenges, prepared by standard pharmaceutical techniques. If a liquid carrier is used, the preparation may be in the form of a soft gelatin capsule, a syrup, an aqueous solution or liquid suspension. Suppositories may be prepared in a conventional manner by mixing the compounds of this invention with a suitable non-irritating excipient which is solid at room temperature but liquid at the rectal temperature. Such materials are cocoa butter and polyethylene glycol. Gels and lotions for topical application may be prepared in conventional manners.

The compounds of Formula I and of the compositions of this invention are to be administered in an amount sufficient to treat inflammation, that is, to reduce inflammation. Advantageously, the compositions will contain the active ingredient; namely, the compounds of Formula I in an amount of from about 0.1 mg. to 50 mg. per kg. body weight per day (5 mg. to 3.5 mg. per patient per day), preferably from about 1 mg. to 15 mg. per kg. body weight per day (50 mg. to 1 g. per patient per day).

The method of treatment of this invention comprises administering to a patient (animal or human), a compound of Formula I, particularly an especially preferred compound admixed with a non-toxic pharmaceutical carrier such as exemplified above. The compounds of Formula I and particularly the especially preferred compounds will be administered in an amount of from 0.1 mg. to 50 mg. per kg. body weight per day, preferably from about 1 mg. to about 15 mg. per kg. body weight per day. The most rapid and effective anti-inflammatory effect is obtained from oral administration of a daily dosage of from about 1 to 15 mg. per kg. per day. It should be understood, however, that although preferred dosage ranges are given, the dose level for any particular patient depends upon the activity of the specific compound employed. Also many other factors that modify the actions of drugs will be taken into account by those skilled in the art in the therapeutic use of medicinal agents, particularly those of Formula I, for example, age, body weight, sex, diet, time of administration, route of administration, rate of excretion, drug combination, reaction sensitivities and severity of the particular disease.

3-Indenyl acetic acid compounds are known from U.S. Pat. No. 3,654,349 issued Apr. 4, 1972. These compounds differ structurally from the 3-indenyl methane sulfonic acid compounds of this invention in that the 3-position of the indene contains a methane sulfonic acid rather than an acetic acid and are prepared by an overall different process.

The following examples are given by way of illustration.

EXAMPLE 1

5-Fluoro-2-methyl-1-(p-methylsulfinylbenzylidene)-indenyl-3-methane sulfonic acid A. 5-Fluoro-2-methylindenyl-3-methylamine 5-Fluoro-2-methylindenyl-3-acetic acid (0.12 mole) is dissolved in acetone (dry 270 ml.) and triethylamine (0.0124 mole) is added with stirring i-butyl chloroformate is then added (0.12 mole). The precipitate is collected after 10 minutes and the triethylamine hydrochloride rinsed out with acetone (50 ml.). Sodium azide (0.127 mole) in water (50 ml.) is added over 10 minutes to the salt in acetone. After 2 hours at room temperature ether (2 liter) and water (1 liter) are added and the mixture separated. The ether layer is washed with water (2 × 100 ml.) separated, dried ($MgSO_4$), filtered and evaporated to an oil. This oil is heated at 100° C with stirring for 5 minutes alone and then with benzyl alcohol (35 ml.) in benzene (500 ml.) at reflux for 3 hours. The solvents are removed under vacuum and the crude product is catalytically reduced in methanol (150 ml.) over Pd/c (5%) (4 g.) and concentrated hydrochloric acid (3 ml.) at room temperature. After removing the catalyst, the solution is extracted with chloroform (3 × 40 ml.) from water (50 ml.) and more 2.5N HCl (70 ml.). The aqueous solution is made basic with saturated sodium bicarbonate solution and extracted with ethyl acetate (4 × 100 ml.), separated and washed with $H_2O$ (2 × 20 ml.). The organic layer is dried ($MgSO_4$), filtered and evaporated to dryness to give the crystalline amine.

B. 5-Fluoro-2-methylindenyl-3-methanol

The above amine (0.1 mole) is dissolved in 2.5N hydrochloric acid (50 ml.) and the solution cooled and stirred in an ice bath at 0° C while 10% aqueous sodium nitrite is added slowly (0.15 mole). The solution is then heated to 60° C with stirring for 1 hour and the alcohol extracted with chloroform (2 × 50 ml.). The chloroform layer is separated, dried ($MgSO_4$), filtered and evaporated to give the crystalline alcohol.

C. 5-Fluoro-2-methylindenyl-3-methylchloride

The above alcohol (0.1 mole) in benzene (50 ml.) and thionyl chloride (0.11 mole) is refluxed for 1 hour and the solution then evaporated to give an oil.

D. 5-Fluoro-2-methylindenyl-3-methyl-5-thiouronium chloride

The above chloro compound (0.1 mole) in isopropanol (100 ml.) is stirred and refluxed with thiourea (0.11 mole) for 3 hours. The 5-thiouronium chloride is precipitated as it is formed and is used as is.

E. 5-Fluoro-2-methylindenyl-3-methylmercaptan

The above thiouronium salt (0.1 mole) is stirred and refluxed under nitrogen in aqueous alcoholic potassium hydroxide (1:1 10% 100 ml.) for 4 hours. The alcohol is evaporated off under reduced pressure and the gummy material extracted into ether (2 × 50 ml.). Evaporation of the ether gave the crystalline mercaptan.

F. 5-Fluoro-2-methylindenyl-3-methylsulfonic acid

The above mercaptan (0.1 mole) in isopropanol (300 ml.) is oxidized with 30% hydrogen peroxide (100 ml.) at room temperature for 24 hours. The isopropanol is evaporated off and the aqueous layer neutralized with sodium bicarbonate. The aqueous layer is extracted with ethyl acetate (3 × 100 ml.), acidified with concentrated hydrochloric acid and again extracted with ethyl acetate (2 × 100 ml.). The ethyl acetate solution is dried ($MgSO_4$), filtered and evaporated to dryness to give the crystalline sulfonic acid.

G. 5-Fluoro-2-methyl-1-(p-methylsulfinylbenzylidene) indenyl-3-methane sulfonic acid 5-Fluoro-2-methyl-indenyl-3-methane sulfonic acid (5.0 mmole) is dissolved in 10 ml. of dry pyridine followed by p-methylsulfinylbenzaldehyde (5.0 mmole). The flask is placed under nitrogen and Triton B (5.1 mmole) in methanol is added. The reaction mixture is allowed to stand overnight and then water (3 ml.) is added. After standing for 15 minutes, it is poured into an excess of water. The organics are extracted with ether (2 × 50 ml.). The aqueous phase is added to 10% HCl ice. The precipitated material is extracted into methylene chloride and dried (MgSO$_4$). The solution is filtered and the solvent removed. The product is recrystallized from benzene to yield the desired compound.

Similarly when benzaldehyde, p-methylthiobenzaldehyde, p-methylsulfonylbenzaldehyde, p-bromobenzaldehyde, p-chlorobenzaldehyde, m-chlorobenzaldehyde, p-fluorobenzaldehyde, p-ethylthiobenzaldehyde, p-butylthiobenzaldehyde, m-nitrobenzaldehyde, m-diethylaminobenzaldehyde, p-methylbenzaldehyde, p-methoxybenzaldehyde, p-ethylsulfinylbenzaldehyde, or p-butylsulfinylbenzaldehyde, is used on an equivalent amount in place of p-methylsulfinylbenzaldehyde in 1G above, there is obtained the corresponding appropriately 1-substituted 3-indenyl methane sulfonic acid compound.

Similarly when an equivalent amount of
2-methyl-3-indenyl acetic acid,
5-hydroxy-2-methyl-3-indenyl acetic acid,
5-methoxy-2-methyl-3-indenyl acetic acid,
5-cyano-2-methyl-3-indenyl acetic acid,
5-fluoro-3-indenyl acetic acid,
5,6-dichloro-2-methyl-3-indenyl acetic acid,
5-bromo-2-methyl-3-indenyl acetic acid,
5-chloro-2-methyl-3-indenyl acetic acid,
5-fluoro-2-methyl-3-indenyl acetic acid,
5-trifluoromethyl-2-methyl-3-indenyl acetic acid,
5-methyl-2-methyl-3-indenyl acetic acid,
5-propyl-2-methyl-3-indenyl acetic acid,
5,7-difluoro-2-methyl-3-indenyl acetic acid,
5-dimethylamino-2-methyl-3-indenyl acetic acid,
5-dipropylamino-2-methyl-3-indenyl acetic acid,
5-allyloxy-2-methyl-3-indenyl acetic acid,
5-methoxy-6-fluoro-2-methyl-3-indenyl acetic acid,
5-butoxy-2-methyl-3-indenyl acetic acid,
5-methoxy-3-indenyl acetic acid, and
5-dimethylamino-3-indenyl acetic acid
are used in place of 5-fluoro-2-methylindenyl-3-acetic acid in Example 1A, and the product further reacted in accordance with Examples 1 B-G, there is obtained the corresponding substituted indenyl-3-methane sulfonic acid.

EXAMPLE 2

5-Fluoro-2-methyl-1-(4'-methylsulfinylcinnamylidenyl)-indenyl-3-methane sulfonic acid To a solution of 0.02 moles of 5-fluoro-2-methylindenyl-3-methylsulfonic acid in methanol (60 ml.) is added sodium methoxide (2.16 g., 0.04 mole) and after solution p-methylsulfinylcinnamaldehyde (0.02 mole). The mixture is heated at reflux for 5 hours, cooled, poured into ether-water. The water layer is acidified and extracted with ether, dried (MgSO$_4$) and concentrated to an oil in vacuo. The oil is taken up in methylene chloride and chromatographed on silica gel and eluted with ethyl acetate. The fractions of eluate are concentrated to yield 5-fluoro-2-methyl-1-(4'-methylsulfinylcinnamylidenyl)-indenyl-3-methane sulfonic acid.

Similarly when an equivalent amount of the aldehyde of Table I below is used in place of 4-methylsulfinylcinnamaldehyde in the above procedure, the corresponding 1-substituted-2-methyl-5-fluoro-indenyl-3-methanesulfonic acid is obtained.

TABLE I

α-tolualdehyde
cinnamaldehyde
hydrocinnamaldehyde
2-methoxycinnamaldehyde
4-methoxycinnamaldehyde
4-ethoxycinnamaldehyde
3,4-dimethoxycinnamaldehyde
4-methylcinnamaldehyde
4-t-butylcinnamaldehyde
2-nitrocinnamaldehyde
3-nitrocinnamaldehyde
4-nitrocinnamaldehyde
4-dimethylaminocinnamaldehyde
4-diethylaminocinnamaldehyde
2-chlorocinnamaldehyde
4-chlorocinnamaldehyde
2,4-dichlorocinnamaldehyde
4-bromocinnamaldehyde
4-methylthiocinnamaldehyde
4-methylsulfinylcinnamaldehyde
4-methylsulfonylcinnamaldehyde
4-chloro-α-methylcinnamaldehyde
4-chloro-2-nitrocinnamaldehyde
4-chloro-3-nitrocinnamaldehyde
5-chloro-2-methylcinnamaldehyde
4-nitro-α-methylcinnamaldehyde
4-nitro-β-methylcinnamaldehyde
4-nitro-β-phenylcinnamaldehyde
α-methylcinnamaldehyde
α-ethylcinnamaldehyde
β-methylcinnamaldehyde
β-ethylcinnamaldehyde
α-β-dimethylcinnamaldehyde
α-pentylcinnamaldehyde
α-cyclopentylcinnamaldehyde
3,4-methylenedioxycinnamaldehyde
3,4,5-trimethoxycinnamaldehyde
3,4-dimethoxy-α-methylcinnamaldehyde
4-isopropyl-α-methylcinnamaldehyde
4-methoxyhydrocinnamaldehyde
2-methylhydrocinnamaldehyde
4-methylhydrocinnamaldehyde
4-sec butylhydrocinnamaldehyde
4-nitrohydrocinnamaldehyde
4-chlorohydrocinnamaldehyde
4-methylthiohydrocinnamaldehyde
4-methylsulfinylhydrocinnamaldehyde
4-methylsulfonylhydrocinnamaldehyde
4-nitro-α-methylhydrocinnamaldehyde
4-nitro-β-methylhydrocinnamaldehyde
4-chloro-α-methylhydrocinnamaldehyde
4-chloro-β-methylhydrocinnamaldehyde
α-methylhydrocinnamaldehyde
β-methylhydrocinnamaldehyde
α,α-dimethylhydrocinnamaldehyde
4-chloro-α-tolualdehyde
4-methoxy-α-tolualdehyde
4-methylthio-α-tolualdehyde α-ethyl-α-tolualdehyde
4-nitro-α-methyl-α-tolualdehyde
4-chloro-α-methyl-α-tolualdehyde
4-phenylbutanal
4-phenyl-2-butanal
2'-thienylacetaldehyde
β-(2'-thienyl)propenal
β-(2'-thienyl)propanal
3'-pyridylacetaldehyde
4'-pyridylacetaldehyde
2'-pyridylacetaldehyde
2'-furylacetaldehyde
5'-chloro-2'-thienylacetaldehyde
α-naphthylacetaldehyde
β-naphthylacetaldehyde
β-(2'-furyl)propenal
β-(2'-pyridyl)propenal
β-(α'-naphthyl)propenal
β-(3'-pyridyl)propenal
β-(4'-pyridyl)propenal
β-(2'-furyl)propanal
β-(2'-pyridyl)propanal
β-α'-naphthyl)propanal
β-(2'-quinolyl)propanal
β-(2'-pyrrolidinyl)propanal
β-(2'-benzofuranyl)propanal
β-(2'-quinolyl)propenal
β-(2'-pyrrolidinyl)propenal
β-(2'-naphthyl)propenal
B,β-diphenylpropenal
2'-indanacetaldehyde
β-(2'-benzothiazole)propenal
β-(3'-nitro-2'-thienyl)propenal
β-(1'-methyl-2'-pyrrolyl)propenal
β-(1'-methyl-2'-pyridyl)propenal Similarly when an equivalent amount of the other substituted indenyl-3-methylsulfonic acids obtained from Example 1 are used in the above example, there is obtained the corresponding substituted-1-(4'-methylsulfinylcinnamylidenyl)-indenyl-3-methanesulfonic acid.

EXAMPLE 3

A. (3-Chloro-4-methylthio)-phenylpropargaldehyde

A mixture of 3-chloro-4-methylthiocinnamaldehyde (2.0 mole) and acetic acid (1.5 liter) is stirred vigorously while bromine (320 g., 2.0 mole) is added dropwise at 25° C. Powdered anhydrous potassium carbonate is added at 25° C. When the evolution of gas stops, the mixture is refluxed for 30 minutes, cooled and poured into cold water (2.5 liters). The mixture is cooled to 0°–5° C with stirring and stirred at this temperature overnight. The precipitate is separated by filtration without drying and crystallized from ethanol-water. 3-Chloro-4-methylthio-α-bromocinnamaldehyde is filtered, washed and dried in air.

The aldehyde (1.6 mole), methyl orthoformate (244 g., 2.3 mole), absolute ethanol (320 ml.) and ammonium chloride (4.0 g.) are refluxed for 30 minutes, low boiling components distilled at atmospheric pressure and distilled in vacuo to yield 2-bromo 1,1-dimethoxy-3-(3'-chloro-4'-methylthiophenyl)-2-propene. To this compound (1.35 mole) is added potassium hydroxide (132 g., 2.0 moles) in methanol (1400 ml.). The mixture is refluxed for 3 hours and poured into water (11.3 liters). The mixture is extracted with chloroform (3 × 1.5 liter), the combined chloroform extracts washed with water (3 × 660 ml.) and dried (Na₂SO₄). The chloroform is distilled and the residue fractionated in vacuo to obtain 1,1-dimethoxy-(3'-chloro-4'-methylthiophenyl)-2-propyne. This compound (1.0 mole) is added to water (1 liter) containing concentrated sulfuric acid (70 ml.) and the mixture is heated on the steam bath for 30 minutes with occasional mixing. The mixture is extracted with ether (3 × 750 ml.), the ether extract washed with water and saturated salt solution, dried (Na₂SO₄) and concentrated to an oil at atmospheric pressure. The oil is distilled in vacuo to yield (3-chloro-4-methylthio)-phenyl-propargaldehyde.

B. cis-and trans-5-Fluoro-2-methyl-1-(3'-chloro-4'-methyl-thiophenylpropargylidene)-indenyl-3-methane sulfonic acid (3-Chloro-4-methylthio)-phenylpropargaldehyde (0.2 mole) and 5-fluoro-2-methyl-indenyl-3-methane sulfonic acid (0.2 mole) are condensed by the method of Example 2 to yield the subject compound.

Similarly when an equivalent amount of the other indenyl-3-methane sulfonic acid compounds obtained from Example 1 are used in place of 5-fluoro-2-methyl-indenyl-3-methane sulfonic acid in the above example, there is obtained the corresponding 1-(3'-chloro-4'-methyl-thiophenylpropargylidene) substituted indenyl-3-methane sulfonic acid compounds.

EXAMPLE 4

5-Fluoro-2-methyl-1-(p-methylthiophenoxymethylidene)-3-indenyl methane sulfonic acid

A. Ethyl 5-fluoro-2-methyl-3-indenyl methane sulfonate

A mixture of 0.1 mole of 5-fluoro-2-methyl-3-indenyl methane sulfonic acid, 0.2 gm. of p-toluene sulfonic acid, 100 ml. of absolute ethanol and 75 ml. of dry benzene is refluxed on a steam bath while slowly distilling the solvent. After 17 hours the residual solvent is removed under reduced pressure. The residue is slurried in aqueous sodium bicarbonate and then with water until neutral.

B. t-Butyl 5-fluoro-2-methyl-3-indenyl methane sulfonate

Ethyl 5-fluoro-2-methyl-3-indenyl methane sulfonate (1.0 mole), t-butyl acetate (700 g., 6.0 mole) and sodium methoxide (108 g., 2 mole) under nitrogen are stirred and refluxed at 10:1 ratio through a 1.5 foot column packed with glass ⅛ inch helices. The mixture is distilled for 18 hours and 250 ml. of distillate is collected. The excess of t-butylacetate is distilled in vacuo and the residue is taken up in methylene chloride, filtered through diatomaceous earth then through acid-washed alumina. The methylene chloride is removed and the residue crystallized from acetone-n-hexane to yield t-butyl 5-fluoro-2-methyl-3-indenyl methane sulfonate.

C. t-Butyl 5-fluoro-1-hydroxymethylene-2-methyl-3-indenyl methane sulfonate, Sodium Salt To a mixture of t-butyl 5-fluoro-2-methyl-3-indenyl methane sulfonate (0.2 mole) in benzene (500 ml.) and ethylformate (74.1 g., 1.0 mole) is added oil-free sodium hydride (7.2 g., 0.3 mole). The mixture is stirred at room temperature 1 hour each day for 2 days. Any remaining sodium hydride is decomposed by the addition of methanol (20 ml.) in ether (100 ml.). The salt is filtered, washed with ether and dried in vacuo.

D. cis- and trans-t-Butyl-5-fluoro-2-methyl-1-(p-methyl-thio-phenoxymethylidene)-3-indenyl methane sulfonate The sodium salt (0.01 mole) from Example 4C in dimethoxyethane (200 ml.) is heated at reflux with stirring for 15 hours with p-methylthiophenyliodide (25.0 g., 0.01 mole). The mixture is concentrated in vacuo to remove solvent, taken up in methylene chloride-water, the layers separated and the water layer extracted with methylene chloride (2 × 100 ml.). The combined methylene chloride layers are concentrated to ⅓ volume and chromatographed over silica gel and eluted by methanolic chloroform to separate cis- and trans- isomers.

E. cis-5-Fluoro-2-methyl-1-(p-methylthiophenoxymethylidene)-3-indenyl methane sulfonic acid The product of Step D above is reacted in accordance with Example 1 A-D to yield the subject product.

Similarly when an equivalent amount of p-methylsulfinylphenyliodide is used in place of p-methylthiophenyliodide in Example 4D above, there is obtained the corresponding 1-(p-methylsulfinylphenoxymethylidene) compound.

EXAMPLE 5

A mixture of 260 parts of 5-fluoro-2-methyl-1-(p-methylsulfinylbenzylidene)-indenyl-3-methane sulfonic acid and 25 parts of lactose is granulated with suitable water and to this is added 100 parts of maize starch. The mass is passed through a 16 mesh screen. The granules are dried at a temperature below 60° C. The dry granules are passed through a 16 mesh screen and mixed with 3.8 parts of magnesium stearate. They are then compressed into tablets suitable for oral administration.

What is claimed is:

1. A compound of the formula:

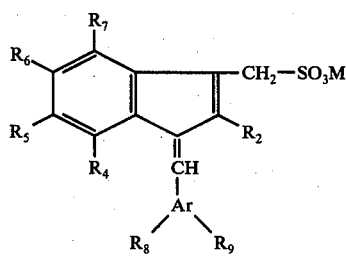

wherein:
$R_2$ is hydrogen or $C_{1-5}$ loweralkyl;
$R_4$, $R_5$, $R_7$, and $R_8$ are hydrogen;
$R_6$ is hydrogen, halo, $C_{1-5}$ loweralkyl,
$R_9$ is hydrogen, chloro, bromo, fluoro, $C_{1-5}$ loweralkylthio, or $C_{1-5}$ loweralkylsulfinyl;
Ar is phenyl; and
M is hydrogen.

2. The compound of claim 1 wherein:
$R_2$ is methyl;
$R_6$ is halo, and
$R_9$ is methylsulfinyl.

3. The compound of claim 2 wherein $R_6$ is fluoro.

4. The compound of claim 1 wherein:
$R_2$ is methyl;
$R_6$ is halo; and
$R_9$ is methylthio.

5. A pharmaceutical composition comprising as an active ingredient 5 mg. to 3.5 grams of a compound of the formula:

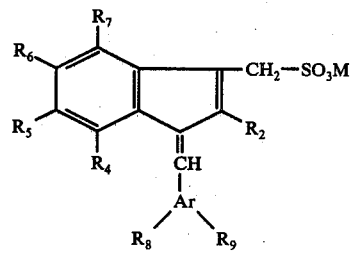

wherein:
$R_2$ is hydrogen or $C_{1-5}$ loweralkyl;
$R_4$, $R_5$, $R_7$ and $R_8$ are each hydrogen;
$R_6$ is hydrogen, halo, $C_{1-5}$ loweralkyl;
$R_9$ is hydrogen, chloro, bromo, fluoro, $C_{1-5}$ loweralkylthio, or $C_{1-5}$ loweralkylsulfinyl;
Ar is phenyl; and
M is hydrogen.

6. The composition of claim 5 wherein:
$R_2$ is methyl;
$R_6$ is halo, and
$R_9$ is methylsulfinyl.

7. The composition of claim 6 wherein $R_6$ is fluoro.

8. The composition of claim 5 wherein:
$R_2$ is methyl;
$R_6$ is halo, and
$R_9$ is methylthio.

9. A method of treating pain, fever and inflammation which comprises administering to a patient an effective amount of a compound of the formula:

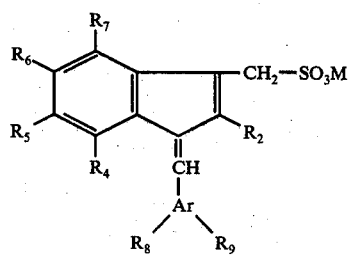

wherein:
$R_2$ is hydrogen or $C_{1-5}$ loweralkyl;
$R_4$, $R_5$, $R_7$ and $R_8$ are each hydrogen;
$R_6$ is hydrogen, halo, $C_{1-5}$ loweralkyl,
$R_9$ is hydrogen, chloro, bromo, fluoro, $C_{1-5}$ loweralkylthio, or $C_{1-5}$ loweralkylsulfinyl;
Ar is phenyl; and
M is hydrogen.

10. The method of claim 9 wherein:
$R_2$ is methyl;
$R_6$ is halo, and
$R_9$ is methylsulfinyl.

11. The method of claim 10 wherein $R_6$ is fluoro.

12. The method of claim 9 wherein:
$R_2$ is methyl;
$R_6$ is halo, and
$R_9$ is methylthio.

* * * * *